(12) United States Patent
Johannison

(10) Patent No.: US 8,998,863 B2
(45) Date of Patent: Apr. 7, 2015

(54) APPARATUS AND METHOD FOR CONTROLLING THE NEGATIVE PRESSURE IN A WOUND

(75) Inventor: Ulf Johannison, Landvetter (SE)

(73) Assignee: Mölnlycke Health Care AB, Göteborg (SE)

( * ) Notice: Subject to any disclaimer, the term of this patent is extended or adjusted under 35 U.S.C. 154(b) by 480 days.

(21) Appl. No.: 13/497,200

(22) PCT Filed: Sep. 21, 2010

(86) PCT No.: PCT/SE2010/051009
§ 371 (c)(1),
(2), (4) Date: Mar. 20, 2012

(87) PCT Pub. No.: WO2011/037524
PCT Pub. Date: Mar. 31, 2011

(65) Prior Publication Data
US 2012/0184930 A1 Jul. 19, 2012

(30) Foreign Application Priority Data

Sep. 22, 2009 (SE) ...................................... 0901223

(51) Int. Cl.
*A61M 1/00* (2006.01)
*A61M 27/00* (2006.01)

(52) U.S. Cl.
CPC .............. *A61M 27/00* (2013.01); *A61M 1/0031* (2013.01); *A61M 1/0084* (2013.01); *A61M 1/0088* (2013.01); *A61M 2205/18* (2013.01); *A61M 1/0052* (2014.02); *A61M 1/0096* (2014.02)

(58) Field of Classification Search
CPC ................ A61F 13/84; A61F 13/4805; A61F 2013/00174; A61F 2013/00536; A61F 2014/0091; A61L 15/46; A61L 2300/404; A61M 1/0005; A61M 1/001; A61M 1/0013; A61M 1/0023; A61M 1/0088; A61M 27/00; A61M 2001/0017; A61M 2001/0052
USPC .................................. 604/304, 305, 313, 319
See application file for complete search history.

(56) References Cited

U.S. PATENT DOCUMENTS 3,572,340 A  3/1971 Lloyd ........................... 128/278
3,742,952 A  7/1973 Magers ......................... 128/278
(Continued)

FOREIGN PATENT DOCUMENTS

CN  101208115 A  6/2008
EP  0865304      7/2001
(Continued)

OTHER PUBLICATIONS

Chariker, et al. "Effective Management of Incisional and Cutaneous Fistulae with Closed Suction Wound Drainage." Journal of Contemp. Surg., Jun. 1989, vol. 34, pp. 59-63.
(Continued)

*Primary Examiner* — Melanie Hand
(74) *Attorney, Agent, or Firm* — Ballard Spahr LLP

(57) ABSTRACT

An apparatus and method are provided for treating wound with negative pressure. The apparatus includes a wound cover, a first pump for providing said negative pressure at a chosen pressure level to the wound, a canister, a first conduit between the wound cover and the canister, first means for measuring the pressure within the canister, and a second conduit which connects the canister with the first pump. A circulating pump is arranged to intermittently transport a gas volume from the canister to the wound region via a third conduit and back to the canister via the first conduit in order to press out possible exudates from the first conduit to the canister. A second means analyzes the pressure curve over time of said pressure in the canister and a third means indicates by alarm when said pressure curve differs from a normal cyclical form.

15 Claims, 3 Drawing Sheets

(56) References Cited

U.S. PATENT DOCUMENTS

| | | | | |
|---|---|---|---|---|
| 4,382,441 | A | 5/1983 | Svedman | 604/291 |
| 4,525,166 | A | 6/1985 | Leclerc | 604/133 |
| 4,969,880 | A | 11/1990 | Zamierowski | 604/305 |
| 5,358,494 | A | 10/1994 | Svedman | 604/313 |
| 5,636,643 | A | 6/1997 | Argenta | 128/898 |
| 5,645,081 | A | 7/1997 | Argenta | 128/898 |
| 5,971,714 | A * | 10/1999 | Schaffer et al. | 417/44.2 |
| 6,855,135 | B2 | 2/2005 | Lockwood | 604/313 |
| 7,438,705 | B2 | 10/2008 | Karpowicz | 604/326 |
| 7,503,910 | B2 | 3/2009 | Adahan | 604/319 |
| 7,779,625 | B2 | 8/2010 | Joshi | 60/313 |
| 2007/0265586 | A1 | 11/2007 | Joshi | 60/313 |
| 2009/0030383 | A1 | 1/2009 | Larsen | 604/315 |
| 2009/0036754 | A1 * | 2/2009 | Pons et al. | 600/301 |
| 2009/0036873 | A1 | 2/2009 | Nielsen | 604/315 |
| 2009/0326488 | A1 | 12/2009 | Budig | 604/319 |
| 2012/0046625 | A1 | 2/2012 | Johannison | |

FOREIGN PATENT DOCUMENTS

| | | |
|---|---|---|
| WO | WO 2006/025848 | 3/2006 |
| WO | WO 2007/092397 | 8/2007 |
| WO | WO 2008/012278 | 1/2008 |
| WO | WO 2008/039223 | 4/2008 |
| WO | WO 2008/132215 | 11/2008 |
| WO | WO 2008/135997 | 11/2008 |
| WO | WO 2009/002260 | 12/2008 |
| WO | WO 2009/004368 | 1/2009 |
| WO | WO 2009/016195 | 2/2009 |
| WO | WO 2009/016605 | 2/2009 |
| WO | WO 2009/071948 | 6/2009 |
| WO | WO 2009/089390 | 7/2009 |
| WO | WO 2009/114624 | 9/2009 |

OTHER PUBLICATIONS

Davydov, et al. "The Bacteriological and Cytological Assessment of Vacuum Therapy of Purulent Wounds." Vestnik Khirurgii, Oct. 1988, pp. 48-52 (published in English in The Kremlin Papers, Perspectives in Wound Care).

Davydov, et al. "Vacuum Therapy in the Treatment of Purulent Lactation Mastitis." Vestnik Khirurgii, Sep. 1986, pp. 66-70 (published in English in The Kremlin Papers, Perspectives in Wound Care).

Davydov, et al. "Concepts for Clinical Biological Management of the Wound Process in the Treatment of Purulent Wounds using Vacuum Therapy." Vestnik Khirurgii, Feb. 1991, pp. 132-135 (published in English in The Kremlin Papers, Perspectives in Wound Care).

Kostiuchenok, et al. "The Vacuum Effect in the Surgical Treatment of Purulent Wounds." Vestnik Khirurgii, Sep. 1986, pp. 18-21 (published in English in The Kremlin Papers, Perspectives in Wound Care).

Usupov, et al. "Active Wound Draingage." Vestnik Khirurgii, 1987, pp. 42-45 (published in English in The Kremlin Papers, Perspectives in Wound Care).

International Preliminary Report on Patentability issued Mar. 27, 2012 for International Application No. PCT/SE2010/051009, which was filed on Sep. 21, 2010 and which was published as WO 2011/037524 on Mar. 31, 2011 (Inventor—Johannison; Applicant—Molnlycke Health Care AB) (pp. 1-8).

International Search Report and Written Opinion issued Dec. 14, 2010 for International Application No. PCT/SE2010/051009, which was filed on Sep. 21, 2010 and which was published as WO 2011/037524 on Mar. 31, 2011 (Inventor—Johannison; Applicant—Molnlycke Health Care AB) (pp. 1-15).

* cited by examiner

APPARATUS AND METHOD FOR CONTROLLING THE NEGATIVE PRESSURE IN A WOUND

CROSS-REFERENCE TO RELATED APPLICATIONS

The present application is a U.S. National Phase Application of International Application No. PCT/SE2010/051009, filed Sept. 21, 2010, which claims priority to Swedish Patent Application No. 0901223-8, filed Sept. 22, 2009, all of which applications are incorporated herein fully by this reference.

TECHNICAL FIELD

The present invention relates to an apparatus for treating wounds with negative pressure, said apparatus including a wound cover, a first pump for providing said negative pressure at a chosen pressure level to the wound, a canister, a first conduit between the wound cover and the canister, which first conduit is arranged to connect the wound with the canister during use of the apparatus, first means for measuring the pressure within the canister, and a second conduit which connects the canister with the first pump.

The invention also relates to a method for controlling the negative pressure in the wound area with use of an apparatus for treating wound with negative pressure, the method steps includes using a first pump to create a negative pressure at a chosen pressure level within a canister, which is connected with the wound via a first conduit, and measuring the pressure in the canister.

BACKGROUND ART

Healing of wound with negative pressure is today an accepted method for treating difficult and with earlier conventional methods slow-healing wounds.

Drainage of, for example, surgical wounds or other weeping wounds with negative pressure is a standard treatment which has been used for decades. An example of a manual suction pump for this purpose is described in U.S. Pat. No. 3,742,952.

U.S. Pat. No. 3,572,340 describes a pump in the form of an elastically compressible body made of an open-celled foam material, preferably a polyurethane foam, which body also serves as a receptacle for fluid drained from the wound. The pump is said to have a capacity to maintain an negative pressure of 15-80 mmHg for more than 48 hours. A perforated drain is intended to be placed in the wound pocket and is connected to the pump by a tube. A similar device is described in U.S. Pat. No. 4,525,166, in the description of which it is specifically stated that the negative pressure not only drains wound fluid but also draws together the wound edges and stimulates tissue growth and healing of the wound. The two latter publications therefore state that vacuum treatment of wounds stimulates wound healing.

The terms vacuum treatment, treatment with reduced pressure and treatment under negative pressure are used interchangeably in the literature. It should be pointed out that, where these terms are used within this description, treatment at a pressure below normal atmospheric pressure is always meant.

Deep wounds have also been treated with a combination of a rinsing fluid supply and subsequent aspiration. Examples of such devices are described in U.S. Pat. No. 5,358,494 and U.S. Pat. No. 4,382,441.

Extensive studies of the effect of both continuous and intermittent treatment of wounds under negative pressure, i.e. pressure below normal atmospheric pressure, were conducted during the 80's in Russian institutions. It was here demonstrated that slow-healing wounds heal substantially faster with the aid of vacuum treatment compared with conventional treatment methods. It was also shown, inter alia, that treatment with reduced pressure produced a significant antibacterial effect. The said Russian studies are described in articles in the Russian medical journal Vestnik Khirurgii. The articles from the said journal are:
1) Kostiuchenok et al, September 1986, pages 18-21.
2) Davydov et al, September 1986, pages 66-70.
3) Usupov et al, April 1987, pages 42-45.
4) Davydov et al, October 1988, pages 48-52.
5) Davydov et al, February 1991, pages 132-135.

In an article by Chariker et al in the journal Contemporary Surgery, issue 34, June 1989, it is stated that vacuum treatment improves the growth of granulation tissue and the wound contraction of wounds which with conventional treatment are very slow-healing.

Vacuum treatment of wounds is described in for instance U.S. Pat. Nos. 4,969,880, 5,645,081, 5,636,643, 6,855,135 and WO 2006/025848 A2.

In order to get a good wound healing when using negative pressure treatment it is important to control the pressure at the wound, i.e. that the chosen and set pressure of the system is the same as is achieved at the wound.

The therapy pressure, i.e. the pressure at the wound, is affected by several factors, such as the difference of the height levels of the wound and of the canister when there is a liquid column in the suction tube between the wound and the canister. The tube can also be clogged by exudates with high viscosity.

EP 0 865 304 B1 describes an apparatus that in addition to a drainage conduit between the wound cover and the canister includes an additional conduit connecting the wound cover to a pressure detecting means, whereby the pressure substantially at the wound site can be measured. The apparatus according to EP 0 865 304 B1 describes an embodiment which includes a relief valve for admitting ambient air to the wound site via the additional conduit and means for controlling the operation of said relief valve.

U.S. Pat. No. 7,438,705 describes a system in which a reference airflow rate is used for monitoring system operation. Deviation from the reference airflow indicates a change in operation. Deviation to a higher airflow indicates leakage, and drop to lower or no airflow indicates blockage in the system.

SUMMARY OF THE INVENTION

By means of the present invention an improved device of the type mentioned in the introduction has been achieved. The apparatus in accordance with the invention is characterized in that a circulating pump is arranged to intermittently transport a gas volume from the canister to the wound region via a third conduit and back to the canister via the first conduit in order to press out possible exudates from the first conduit to the canister, that a second means is arranged to analyse the pressure curve over time of said pressure in the canister, which pressure curve intermittently is influenced by said transport of the gas volume, and that a third means is arranged to indicate by a visible and/or audible alarm when said pressure curve differs from a normal cyclical form.

An advantage with this solution is that the user gets a clear indication when the first conduit is blocked up with exudates, i.e. with this apparatus one can direct take correct measures to solve the problem. In earlier known apparatus for detecting malfunction one cannot get information that it is precisely a block up in the first conduit that cause the problem.

Another advantage with the above defined apparatus is that consumption of energy is much less when gas is circulated in the system instead of letting in ambient air. When ambient air at atmospheric pressure has been let in it is necessary to again establish therapy pressure which demands a lot of energy and quick consumption of batteries.

A further advantage is less discharge of gas from the apparatus and by that the risk is reduced for letting out odour from the apparatus.

According to an embodiment the invention is further characterized in that that said circulating pump is time controlled and that said circulating pump is arranged to transport said gas volume at regular intervals.

According to an embodiment the invention is characterized in that said circulation pump is controlled by the time required to re-establish the negative pressure to the same level as it was before the last circulation of said gas volume.

According to an embodiment the invention is characterized in that said second means includes a printed circuit board.

According to an embodiment the invention is characterized in that the third means includes a human machine interface with a display.

According to another embodiment the invention is characterized in that the printed circuit board is arranged to control the display for presenting on the display when the first conduit is blocked up, which presentation can be in form of a symbol or in clear text.

According to an embodiment the invention is characterized in that a check valve is arranged in a connecting branch on the wound cover to hinder the gas volume pumped by the circulating pump from reaching the wound.

According to an embodiment the invention is characterized in that said first means for measuring the pressure within the canister is a pressure sensor.

According to an embodiment the invention is further characterized in that said pressure sensor is a piezo-electrical sensor.

The method according to the invention is characterized in that a gas volume is intermittently transported with a circulating pump from the canister towards the wound region via a third conduit and that said gas volume is further directed to the first conduit and back through the first conduit to the canister for pushing possible exudates residing in the first conduit to the canister, that the pressure curve over time of said pressure in the canister is analysed, which pressure curve is intermittently influenced by said transport of the gas volume, and that a visible and/or audible alarm is activated when said pressure curve differs from a normal cyclical form.

The method according to the invention is further characterized in that said gas volume is pushed through the third conduit with said circulating pump at regular time intervals and that the length of said time interval is chosen for setting maximal allowed difference of the negative pressure within the wound relatively the set pressure in the canister.

According to an embodiment the method in accordance with the invention is characterized in that said gas volume is pushed through the third conduit with said circulating pump at time intervals which length can vary, that the length of an individual interval is controlled by the time required to re-establish the negative pressure to the same level as it was before the last circulation of said gas volume.

DETAILED DESCRIPTION

Figure 1:
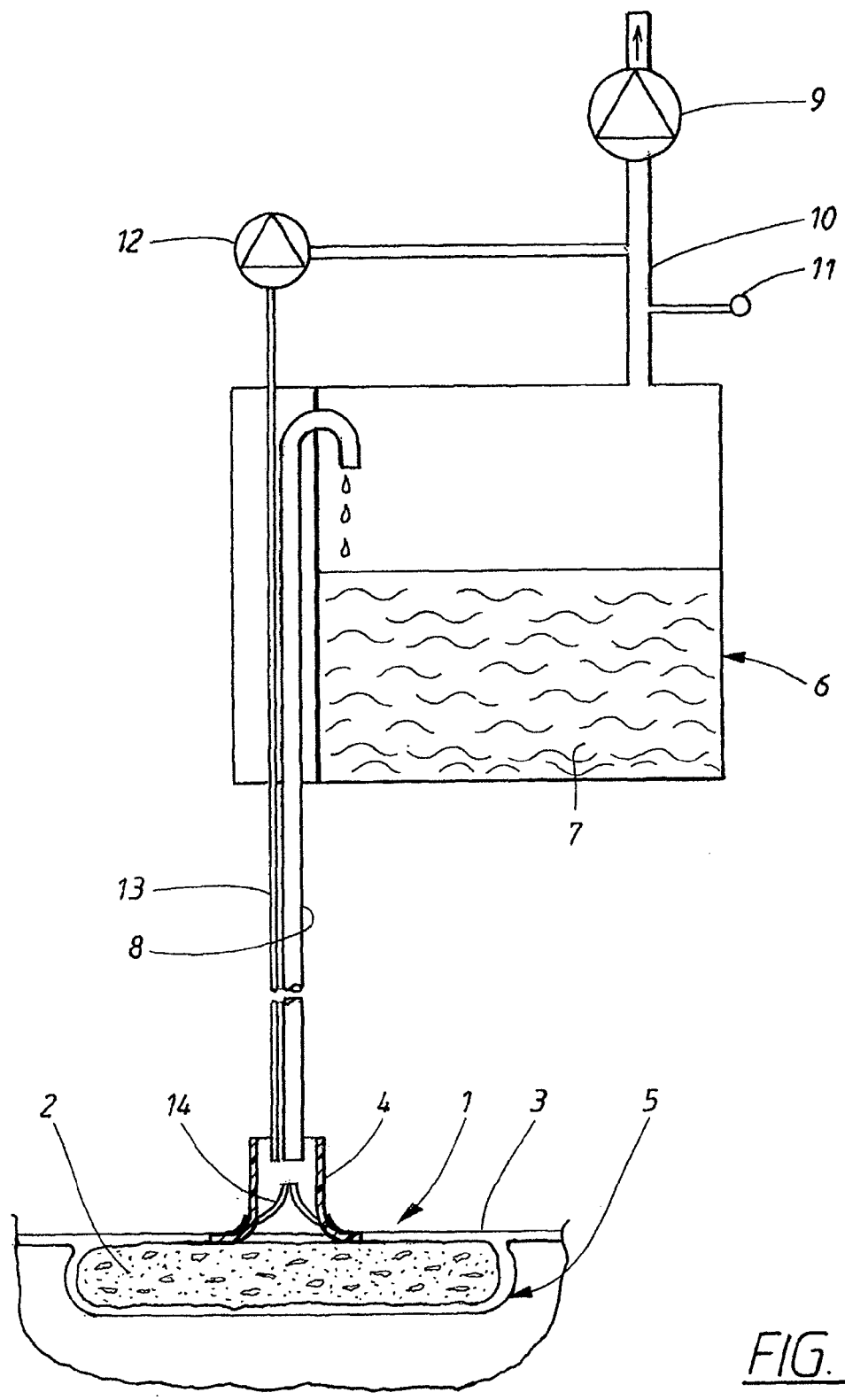
FIG. 1 is a schematic illustration of the apparatus according to the invention.

The apparatus according to the invention includes a wound cover 1, which in the shown embodiment in FIG. 1 comprises a wound filler 2, a sealing film 3 and a connecting branch 4. The wound filler may be open-celled polymeric foam, such as polyurethane foam or polyvinyl alcohol foam having interconnecting cells for distribution of an applied negative pressure over the wound 5. The sealing film 3 can for example be a polyurethane film.

A canister 6 is arranged to collect wound exudates 7, which is sucked from the wound via a first conduit 8. A first pump 9 is arranged to apply the negative pressure in the canister and in the wound area. The pump 9 is connected with the canister via a second conduit 10. A pressure measuring means 11 is arranged as shown in the second conduit for measuring the pressure within the canister. This pressure is the same as the pressure in the wound area when no wound exudates are present in the first conduit.

The apparatus includes a circulating pump 12 for transporting gas from the canister to the wound area via a third conduit 13 and back to the canister via the first conduit 8 with the purpose to pressing out a possible liquid column from the first conduit to the canister. A check valve 14 is arranged in the connecting branch 4 to hinder gas pumped by the circulating pump 12 from reaching the wound area. The check valve can for instance be a duck bill valve. The check valve 14 is arranged to allow gas and wound exudates to be sucked in the direction from the wound to the canister 6.

The negative pressure in the canister is established with the first pump 9. This negative pressure is transferred to the wound via the first tube 8. With the expression negative pressure is meant a pressure below atmospheric pressure. A suitable negative pressure is chosen by the care taker, such as a doctor or a nurse. Depending on the type and state of the wound said negative pressure is set at a suitable level, which normally is chosen between about 50-150 mmHg below atmospheric pressure. The pressure in the canister is measured with the pressure sensor 11. The pressure in the wound is the same as in the canister when no liquid is blocking the first conduit. If there is a height difference between the wound and the canister and a liquid column is blocking the first conduit the pressure in the wound area differs from the negative pressure in the canister. The effect of a liquid column present in the first conduit is that it will decrease the negative pressure in the wound area. A water column that is one meter high corresponds to a pressure difference of approximately 76 mmHg. This value shall be subtracted from the value in the canister to get the negative pressure in the wound. If it is a negative pressure of 100 mmHg in the canister and the water column is one meter then there is a negative pressure in the wound area of only 24 mmHg.

It is not possible to just compensate for the liquid column by setting a higher value for the negative pressure in the canister. The reason for that is that it is not possible to know how much exudates there is in the tube or the difference in height between the wound and the canister, which height also can vary when the patient moves for instance from a lying position to a sitting position.

To minimize this problem it is according to the present invention arranged a circulating pump 12 for transporting gas from the canister to the wound region via the third conduit 13 and back to the canister via the first conduit. The gas transported with the circulating pump enters the connecting branch 4 to the wound cover. The check valve 14 hinders the gas from entering the wound area and the gas is forced up through the first conduit 8 and pressing out a possible liquid column from the first conduit to the canister.

An important advantage with the solution according to the invention is that a very small amount of gas is needed for cleaning the first conduit from exudates. One can therefore chose a very small pump as circulating pump. A suitable pump is a small electric or piezoelectric pump, which in use is very quiet and which consume very little power. A further great benefit with the solution according to the invention is that the chosen negative pressure in the canister is hardly affected by said small amount of gas needed for cleaning the first conduit. To achieve and keep the desired negative pressure it is with the solution according to the present invention possible to choose a small pump as the first pump 9. The pump 9 can be powered by batteries, such as rechargeable batteries. The negative pressure in the canister is, as mentioned above, measured with the pressure sensor 11.

The invention will in the following be described in more detail with reference to the embodiment shown in form of a block diagram in FIG. 2.

Figure 2:
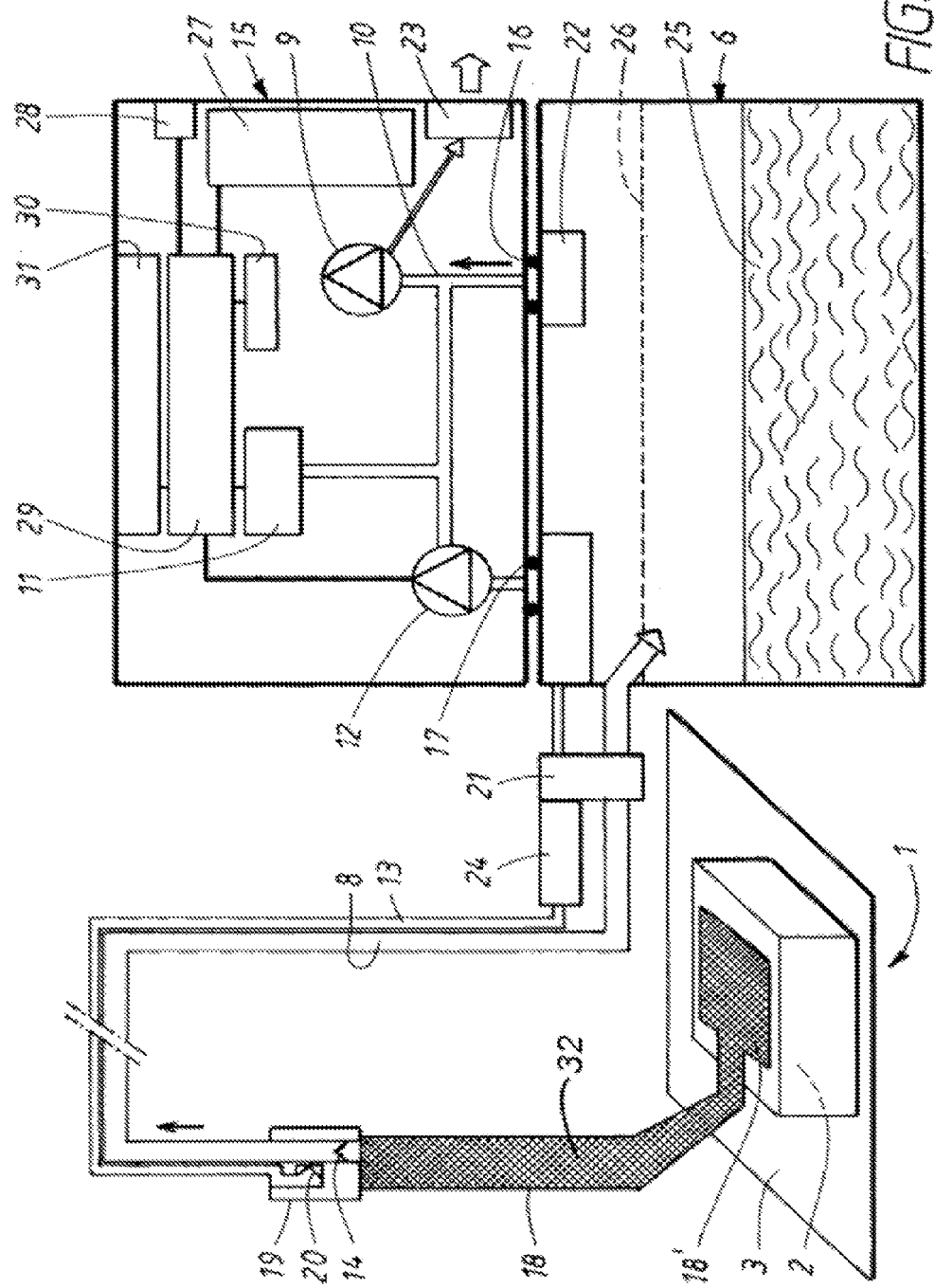
FIG. 2 is a block diagram over a more detailed embodiment of an apparatus according to the invention

Details in FIG. 2 which corresponds to similar details in FIG. 1 have been designated with the same reference number.

The canister 6 is a disposable part of the apparatus according to the invention. The embodiment of the apparatus shown in FIG. 2 includes a control unit 15 which is intended to be reused. The disposable canister 6 is detachably arranged on the control unit. Two washers 16 and 17 are arranged to provide gastight sealing between the canister and the control unit.

The wound cover 1 comprises a wound filler 2 for instance in the form of an open-cell polymer foam and a sealing film 3 arranged over the wound filler and fastened to the skin of the patient. The sealing film 3 is preferably transparent. The open-cell polymer foam has in the drawing been illustrated with dashed lines. A soft tube 18 is arranged to connect at one end to the first conduit 8 at a connector 19. The third conduit 13 is connected to the first conduit in the connector. A check valve 20 is arranged to allow flow from the third conduit to the first conduit and hinder flow of gas and liquid in the opposite direction. The interior of the tube 18 consists of a strand 32 made of an open-pored foam material. The tube casing may consist of two plastic films made of a soft elastic plastic, which plastic films are connected along the edges of the tube to form a casing which runs around the strand 32. At one end of the tube, the plastics films have a widened portion for the formation of the fixing member 18'. One of said plastic films is at the widened portion provided with a central opening, which, when the tube is used, is intended to be placed right in front of an applied hole in the sealing film 3. Said one of the plastics film is provided with a bonding agent for connection to the outer side of the sealing film around the hole made therein. The said bonding agent is expediently constituted by a silicone adhesive, which gives good sealing and prevents leakage at the fixing member. One advantage with silicone adhesive is that the fixing member can be easily detached and refastened to the sealing film should the fixing member end up wrong on the sealing film.

Alternatively, other pressure-sensitive adhesives, such as acrylate, may be used.

A tube of the described kind is soft and pliable and can be of thin configuration. The soft tube is comfortable for the patient and does not give rise to chafes against the skin of the patient when load stresses arise.

The tube 18 can also be made as described in our application WO 2009/002260.

The first and third conduits are connected to the canister via a connector 21.

The negative pressure in the canister 6 is established with the first pump 9. An odour filter 22 with activated carbon is arranged in the canister in front of the second conduit 10 to prevent odour from reaching ambient air. This filter may as well have the capacity to trap contamination particles such as viruses and bacteria. In the embodiment according to FIG. 2 a further filter 23 is arranged after the first pump to further clean gas that is exhausted to ambient air. A silencer may also be included. As described above the circulating pump transport an amount of air from the canister 6 through the third conduit 13 for pushing out a possible liquid column in the first conduit to the canister. As the control unit with the circulating pump will be used repeatedly by different patients a bacteria filter 24 is arranged in the third conduit for preventing that bacteria is transferred from one patient to another.

In the canister 6 is in the disclosed embodiment arranged absorbent material 25 in form of super absorbent material, such as super absorbent powder or fibers bonded to textile material or to thermoplastic fibers. Such an arrangement is advantageous when the apparatus is intended to be portable in order to prevent that liquid exudates in the canister is splashing when the patient moves. A spacer 26 is arranged to prevent that formed superabsorbent gel closes the filter 22.

An indicator, such as an optic indicator (not shown) may be arranged to indicate when the canister is filled with exudates. The canister is an airtight plastic container with a size of approximately 300 ml.

The control unit includes a rechargeable battery 27. The battery charger is marked with 28. A printed circuit board (PCB) 29, includes electronics for control of running of the pumps. An alarm buzzer 30 is connected to the PCB as well as a human machine interface (HMI) 31.

Figure 3:
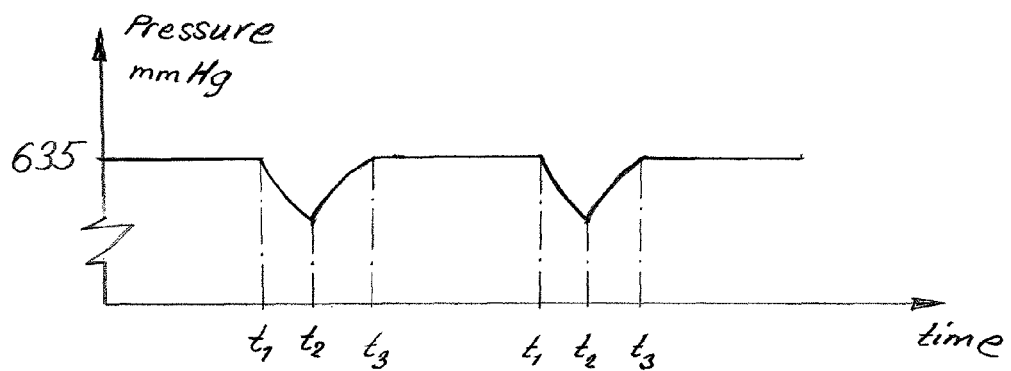
FIG. 3 is a schematic pressure curve over time of the pressure in the canister under normal working condition of the apparatus.

In FIG. 3 is shown a time-pressure curve of the pressure in the canister, which pressure is measured with the pressure sensor 11. The chosen negative pressure is in the illustrated curve 125 mmHg, which means that the negative pressure at the wound is 125 mmHg if the first conduit is free from exudates. A negative pressure of 125 mmHg correlates to a pressure as shown in the graph of 635 mmHg. The circulating pump 12 is arranged to intermittently transport a gas volume from the canister 6 to the wound region via the third conduit 13 and back to the canister via the first conduit. The gas volume needed to clean the first conduit is quite small and the pressure in the canister is therefore not disturbed to such a degree that it will have any practical effect on the desired treatment pressure. On the time pressure curve in FIG. 3 the time $t_1$ indicates the start of the circulating pump and the time $t_2$ the stop of the circulating pump. At $t_2$ the gas volume used to clean the first conduit has been evacuated from the canister. Said gas volume will be transported back to the canister via the first conduit and bring possible exudates in the first conduit to the canister. At the time $t_3$ the earlier evacuated gas volume is back in the canister and the negative pressure in the canister is then back at about 125 mmHg (a pressure level of 635 mmHg as illustrated in FIG. 3). In FIG. 3 the normal course is illustrated, i.e. the first conduit is not blocked up with exudates.

Figure 4:
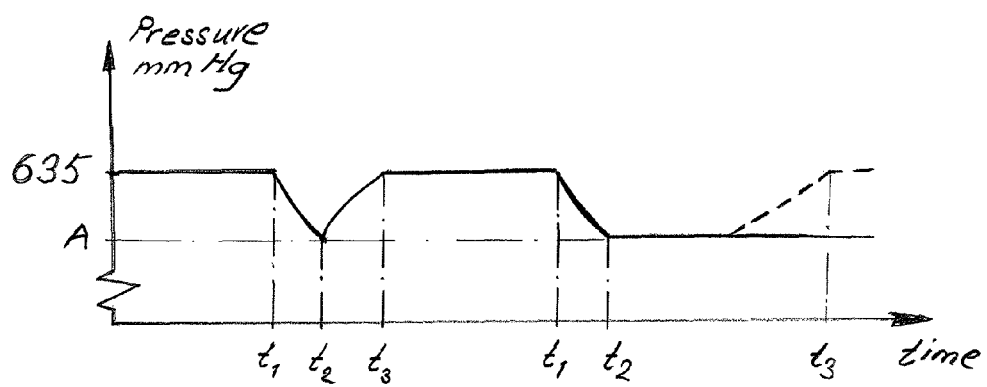
FIG. 4 illustrates schematically the pressure curve over time of the pressure in the canister when there is a block up of the first conduit due to remaining exudates in said conduit.

FIG. 4 shows a time-pressure curve of the pressure in the canister when a block up of the first conduit occurs. When a block up with exudates occurs in the first conduit a change from the normal intermittent course can be seen in the time-pressure curve. The earlier course, i.e. with intermittent drop between the time $t_1$ and $t_2$ and the following return between the time $t_2$ and $t_3$ to the desired pressure as illustrated in FIG. 3 and on the left hand in FIG. 4, is broken. When the first conduit is blocked up with exudates the gas volume evacuated from the canister cannot return to the canister via the first conduit and the negative pressure in the canister remains at level A, i.e. the level after evacuation of said gas volume from the canister. This is illustrated to the right in FIG. 4. The circulating pump 12 also fills the function of a check-valve, i.e. hinder the evacuated gas volume to return from the third conduit 13 back to the canister. If the circulating pump, i.e. said "check-valve", is not entirely air-tight air will ooze back to the canister as illustrated with the dotted line in FIG. 4.

The PCB is arranged to register said time-pressure curve of the pressure in the canister and transfer information to the human machine interface 31 (HMI 31). The HMI 31 includes a display which may be arranged to show a symbol illustrating a blocked conduit when the first conduit is blocked up, i.e. when the time-pressure curve remains at level A as illustrated in FIG. 4.

In addition or alternatively a block up in the first conduit may also be shown in clear text on the display. The alarm buzzer 30 may also be activated when the first conduit is blocked up.

In order to alert the user of some undesirable situations a few further alarms may be arranged in the apparatus. These alarms notify the user when the battery level is low, or if there is a leakage. These alarms may be a sound signal with the buzzer 30 and/or a visible sign on a display on the HMI.

The apparatus is preferably arranged so that the user is able to use the control unit in everyday life. For this purpose there are a number of requirements that regulate the time to charge the batteries, how often the batteries need to be charged, durability, noise vibrations etc. The battery should preferably last at least for twenty-four hours and the time for charging the batteries should preferably not exceed three hours.

The control unit is programmed so that the circulating pump works intermittently. For instance the control unit may be arranged such that said circulation pump is time controlled in order to control the maximal height of a possible liquid column that can be built up in the first conduit during a period when the circulating pump is turned off. The height of such a liquid column that can be built up during such a period depends of course of the amount of wound exudates that is sucked from a wound for a given period and this amount depends of course on several different factors, such as the size, the type and state of the wound.

An alternative solution to intermittently running the circulation pump is to use the time length, $t_2$-$t_3$, required to re-establish the negative pressure to the same level as it was before the last circulation cycle of said gas volume for deciding when to start a new cycle.

The longer the time $t_2$-$t_3$ is the higher is the tendency of clogging and accordingly there is a need to run the circulation pump more often.

If on the other hand the $t_2$-$t_3$ period is short, there is a low tendency of clogging and the circulating cycle frequency can be lower, which in turn can save pump batteries for the pump 12 and energy.

The apparatus and method according to the invention is not limited to the above described embodiments. A number of variants are possible within the scope of the following claims.

The invention claimed is:

1. An apparatus for treating a wound with negative pressure, said apparatus comprising:
    a wound cover;
    a first pump for providing said negative pressure at a chosen pressure level to the wound;
    a canister;
    a first conduit between the wound cover and the canister, wherein the first conduit is arranged to connect the wound with the canister during use of the apparatus;
    first means for measuring the pressure within the canister;
    a second conduit that connects the canister with the first pump;
    a circulating pump; and
    a third conduit that connects the canister and a wound region of the wound, wherein the circulating pump is arranged to intermittently transport a gas volume from the canister to the wound region via the third conduit and back to the canister via the first conduit in order to press out possible exudates from the first conduit to the canister, wherein a second means is arranged to analyze the pressure curve over time of said pressure in the canister, said pressure curve being intermittently influenced by said transport of the gas volume, and wherein a third means is arranged to indicate by an alarm when said pressure curve differs from a normal cyclical form, wherein the alarm is visible, audible, or visible and audible.

2. The apparatus of claim 1, wherein said circulating pump is time controlled and wherein said circulating pump is arranged to transport said gas volume at regular intervals.

3. The apparatus of claim 1, wherein said circulating pump is controlled by the time required to re-establish the negative pressure in the canister to the same level as it was before the last circulation cycle of said gas volume.

4. The apparatus of claim 1, wherein said second means includes a printed circuit board.

5. The apparatus of claim 4, wherein said third means includes a human machine interface with a display.

6. The apparatus of claim 5, wherein the printed circuit board is arranged to control the display for presenting on the display when the first conduit is blocked up, wherein said presentation on the display can be in form of a symbol or in clear text.

7. The apparatus of claim 1, wherein a check valve is arranged in a connecting branch on the wound cover to hinder the gas volume pumped by the circulating pump from reaching the wound.

8. The apparatus of claim 1, wherein said first means for measuring the pressure within the canister is a pressure sensor.

9. The apparatus of claim 8, wherein said pressure sensor is a piezo-electrical sensor.

10. A method for controlling the negative pressure in a wound with the use of an apparatus for treating wounds with negative pressure, the method comprising:
    using a first pump to create a negative pressure at a chosen pressure level within a canister, which is connected with the wound via a first conduit;
    measuring the pressure in the canister;
    intermittently transporting a gas volume with a circulating pump from the canister towards the wound region via a third conduit;
    directing said gas volume to the first conduit and back through the first conduit to the canister for pushing possible wound exudates residing in the first conduit to the canister;

analyzing the pressure curve over time of said pressure in the canister, said pressure curve being intermittently influenced by said transport of the gas volume; and selectively activating an alarm when said pressure curve differs from a normal cyclical form, wherein the alarm is visible, audible, or visible and audible.

11. The method of claim 10, wherein said gas volume is transported through the third conduit with said circulating pump at regular time intervals, and wherein the length of said time interval is chosen for setting maximal allowed difference of the negative pressure within the wound relative to the set pressure in the canister.

12. The method of claim 10, wherein said gas volume is transported through the third conduit with said circulating pump at time intervals of varying length, wherein the length of an individual time interval is controlled by the time required to re-establish the negative pressure to the same level as it was before the last circulation of said gas volume.

13. The apparatus of claim 3, wherein the circulating pump is controlled by the time ($t_2$-$t_3$) required to reestablish the negative pressure in the canister to the same level as it was before the last circulation cycle of said gas volume, wherein $t_2$ represents a time at which the circulating pump is stopped and the gas volume used to clean the first conduit has been evacuated from the canister, and wherein $t_3$ represents the time at which the evacuated gas volume is reintroduced in the canister and the negative pressure in the canister has been reestablished.

14. The method of claim 12, wherein the length of an individual time interval is controlled by the time ($t_2$-$t_3$), wherein $t_2$ represents a time at which the circulating pump is stopped and the gas volume used to clean the first conduit has been evacuated from the canister, and wherein $t_3$ represents the time at which the evacuated gas volume is reintroduced in the canister and the negative pressure in the canister has been reestablished.

15. The apparatus of claim 7, wherein the check valve is arranged in the connecting branch on the wound cover to allow the gas volume pumped by the circulating pump to reach the canister via the first conduit.

* * * * *